United States Patent [19]
Lee et al.

[11] Patent Number: 6,025,475
[45] Date of Patent: Feb. 15, 2000

[54] GROWTH DIFFERENTIATION FACTOR-3

[75] Inventors: Se-Jin Lee; Alexandra C. McPherron, both of Baltimore, Md.

[73] Assignee: The Johns Hopkins University School of Medicine, Baltimore, Md.

[21] Appl. No.: 09/153,733

[22] Filed: Sep. 15, 1998

Related U.S. Application Data

[60] Division of application No. 08/481,377, filed as application No. PCT/US94/00666, Jan. 12, 1994, Pat. No. 5,808,007, which is a continuation-in-part of application No. 08/003,140, Jan. 12, 1993, abandoned.

[51] Int. Cl.[7] .......................... C07K 16/26; C07K 16/24
[52] U.S. Cl. ..................... 530/387.9; 530/388.1; 530/388.15; 530/388.23; 530/388.24
[58] Field of Search .............. 530/387.9, 388.1, 530/388.15, 388.23, 388.24

[56] References Cited

U.S. PATENT DOCUMENTS 5,808,007  9/1998  Lee et al. ................................ 530/399

OTHER PUBLICATIONS

Jones et al., Molecular Endocrinology vol. 6. No. 11, pp. 1961–1968, Nov. 1992.
Jones et al., Development vol. 111, pp. 531–542, 1991.
Wang et al., PNAS, vol. 87, pp. 2220–2224, Mar. 1990.
Wozney et al., Science vol. 242, pp. 1528–1532, Dec. 16, 1988.

*Primary Examiner*—Elizabeth Kemmerer
*Attorney, Agent, or Firm*—Gary, Cary, Ware & Freidenrich LLP; Lisa A. Haile

[57] ABSTRACT

Growth differentiation factor-3 (GDF-3) is disclosed along with its polynucleotide sequence and amino acid sequence. Also disclosed are diagnostic and therapeutic methods of using the GDF-3 polypeptide and polynucleotide sequences.

4 Claims, 9 Drawing Sheets

```
  1  TGAGGGGCTGAGAAGAGCAATTCACACTTGATTAGCTCCCAGGCTCCTGAATTGAGCA         60
 61  GAGGAGGCTAGACCGCTGAGCTGCGCACCCCAGGCTGCTACCCTGGCTCAGACGAC          120
121  CATGCAGCCTTATCAACGGCTTCTGGCTCTTGGTCCTCGTTAACCCTGCCCTGGGG          180
       M  Q  P  Y  Q  R  L  L  A  L  G  F  L  L  L  T  L  P  W  G
181  CCAGACATCCGAGTTCAAGACTCTGACCTTTGCAGTTCTGGATTAGAGAAAGCGCC          240
       Q  T  S  E  F  Q  D  S  D  L  Q  F  L  G  L  E  K  A  P
241  TTCACCTCACAGTTCCAACCTGTGCCTCGCGTCTTAAGGAAATCATCCGGCTCGAGA         300
       S  P  H  R  F  Q  P  V  P  R  V  L  R  K  I  I  R  A  R  E
301  AGCCGCTGCAGCAGCCTGGGCCTCGCAGGACTGTATGCTCGTGAAGAGCTGGGTGTCG        360
       A  A  A  S  G  A  S  Q  D  L  C  Y  V  K  E  L  G  V  R
361  TGGGAACCTGTCCTCCAGCTTCTCCCCAGAAGGTTTTTTCCTAATACACAGAAACCTTT      420
       G  N  L  L  Q  L  L  P  D  Q  G  F  F  L  N  T  Q  K  P  F
421  CCAAGATGGCAGTCTCCTGTCCCAGTCCTAGACTCTGGGCCCATCTGCCATCAAAGAAAA     480
       Q  D  G  S  C  L  Q  K  V  L  Y  F  N  L  S  A  I  K  E  K
481  GGCAAAGTTGACCATGGCCCAGCTGACTCTGGATCTAGGTCCAGTCCTACTATAACCT       540
       A  K  L  T  M  A  Q  L  T  L  D  L  G  P  R  S  Y  Y  N  L
541  GCGACCAGAGCTGGTGGTGGCTTTTCTGCAGATTGCTTTTCTGGTCTGTGCGGGGCGATC    600
       R  P  E  L  V  V  A  L  S  V  V  Q  D  R  G  V  W  G  R  S
601  CCACCCTAAGGTGGGCCGCCTTCTCCTTCGGTCCGTCCCTGGCCCTCAAGGTCAGCT        660
       H  P  K  V  G  R  L  L  F  L  R  S  V  P  G  P  Q  G  Q  L
661  CCAGTTCAACCTGCAGGGTGCGCTTAAGGATTGGAGCAGCAACCGACTGAAGAATTTGA      720
       Q  F  N  L  Q  G  A  L  K  D  W  S  S  N  R  L  K  N  L  D
```

FIG.2a

```
 721  CTTACACTTAGAGATTTTGGTCAAAGAGGACAGATACTTCCAGGGTAACTGTCCAGCCCGA   780
      L  H  L  E  I  L  V  K  E  D  R  Y  S  R  V  T  V  Q  P  E
 781  GAACCCCTGTGACCCGCTCCTCTACACTGCCTCGCTGCTGGTGGTAACCCTCAA          840
      N  P  C  D  P  L  L  R  S  L  H  A  S  L  L  V  V  T  L  N
 841  TCCTAAACACTGTCATCCCTTCTTCCAGAAAAAGGAGGGGCCATCTCTGTCCCAAGG      900
      P  K  H  C  H  P  S  S [R  K  R] A  A  I  S  V  P  K  G
 901  TTTCGTAGGAACTTCTGCCACCGTCACCGTCATCAGCTGTTCATCAACTTCCAGGACCTGGGTG  960
      F  C  R  N  F  C  H  R  H  Q  L  F  I  N  F  Q  D  L  G  W
 961  GCACAAGTGGGTCATGCGCCCCTAAGGCAACCCCCTAAGGCAAATTACTGTCATGGAGAGTGCCC 1020
      H  K  W  V  I  A  P  K  G  F  M  A  N  Y  C  H  G  E  C  P
1021  CTTCTCAATGACCACGTATTTAAATAGTTCCAATTATGCTTTCATGCAGCTCTGATGCA     1080
      F  S  M  T  T  Y  L [N  S  S] N  Y  A  F  M  Q  A  L  M  H
1081  TATGGCTGACCCAGGTCCCCACCAAGCTCTGCCCATCTC                          1140
      M  A  D  P  K  V  P  K  A  V  C  V  P  T  K  L  S  P  I  S
1141  CATGCTCTATCAGGATGATAACAGTGATGAAGACATGGTAGT                       1200
      M  L  Y  Q  D  S  D  K  N  V  I  L  R  H  Y  E  D  M  V  V
1201  CGATGAGTGTGGGTGTCTCGGGACTAGGTGTCTAGGGAGTGTGCTAGGGTAAATCC         1260
      D  E  C  G  C  G  *
1261  TTTAATAAAACTACCACCCCC  1280
```

| | GDF-3 | GDF-9 | GDF-1 | Vg-1 | Vgr-1 | OP-1 | BMP-5 | 60A | BMP-2 | BMP-4 | DPP |
|---|---|---|---|---|---|---|---|---|---|---|---|
| TGF-β5 | 36 | 25 | 32 | 34 | 37 | 36 | 36 | 36 | 35 | 33 | 35 |
| TGF-β4 | 33 | 22 | 34 | 32 | 39 | 37 | 36 | 38 | 33 | 32 | 33 |
| TGF-β3 | 32 | 25 | 33 | 37 | 39 | 38 | 36 | 40 | 36 | 35 | 35 |
| TGF-β2 | 31 | 25 | 32 | 36 | 37 | 38 | 35 | 39 | 34 | 33 | 35 |
| TGF-β1 | 36 | 23 | 33 | 34 | 35 | 34 | 34 | 38 | 35 | 34 | 35 |
| INHIBIN βB | 41 | 31 | 35 | 37 | 41 | 42 | 37 | 39 | 42 | 42 | 42 |
| INHIBIN βA | 42 | 30 | 37 | 44 | 44 | 43 | 43 | 36 | 42 | 41 | 39 |
| INHIBIN α | 25 | 27 | 23 | 22 | 25 | 24 | 24 | 24 | 22 | 22 | 19 |
| MIS | 22 | 21 | 34 | 30 | 24 | 27 | 24 | 25 | 27 | 27 | 25 |
| BMP-3 | 42 | 29 | 42 | 49 | 44 | 42 | 43 | 41 | 48 | 47 | 43 |
| DPP | 47 | 32 | 41 | 48 | 59 | 58 | 57 | 54 | 74 | 75 | 100 |
| BMP-4 | 50 | 34 | 43 | 56 | 60 | 58 | 59 | 54 | 92 | 100 | - |
| BMP-2 | 53 | 33 | 42 | 58 | 61 | 60 | 61 | 57 | 100 | - | - |
| 60A | 47 | 30 | 41 | 51 | 71 | 69 | 74 | 100 | - | - | - |
| BMP-5 | 50 | 31 | 46 | 56 | 91 | 88 | 100 | - | - | - | - |
| OP-1 | 50 | 30 | 47 | 57 | 87 | 100 | - | - | - | - | - |
| Vgr-1 | 53 | 31 | 46 | 58 | 100 | - | - | - | - | - | - |
| Vg-1 | 57 | 30 | 57 | 100 | - | - | - | - | - | - | - |
| GDF-1 | 50 | 27 | 100 | - | - | - | - | - | - | - | - |
| GDF-9 | 33 | 100 | - | - | - | - | - | - | - | - | - |
| GDF-3 | 100 | - | - | - | - | - | - | - | - | - | - |

FIG. 4a

|  | BMP-3 | MIS | INHIBIN α | INHIBIN βA | INHIBIN βB | TGF-β1 | TGF-β2 | TGF-β3 | TGF-β4 | TGF-β5 |
|---|---|---|---|---|---|---|---|---|---|---|
| TGF-β5 | 30 | 26 | 24 | 36 | 28 | 82 | 70 | 73 | 79 | 100 |
| TGF-β4 | 27 | 29 | 24 | 33 | 30 | 86 | 68 | 74 | 100 | - |
| TGF-β3 | 32 | 25 | 24 | 36 | 37 | 78 | 82 | 100 | - | - |
| TGF-β2 | 32 | 23 | 22 | 37 | 34 | 74 | 100 | - | - | - |
| TGF-β1 | 32 | 28 | 23 | 41 | 35 | 100 | - | - | - | - |
| INHIBIN βB | 37 | 25 | 25 | 63 | 100 | - | - | - | - | - |
| INHIBIN βA | 36 | 24 | 26 | 100 | - | - | - | - | - | - |
| INHIBIN α | 29 | 18 | 100 | - | - | - | - | - | - | - |
| MIS | 30 | 100 | - | - | - | - | - | - | - | - |
| BMP-3 | 100 | - | - | - | - | - | - | - | - | - |
| DPP | - | - | - | - | - | - | - | - | - | - |
| BMP-4 | - | - | - | - | - | - | - | - | - | - |
| BMP-2 | - | - | - | - | - | - | - | - | - | - |
| 60A | - | - | - | - | - | - | - | - | - | - |
| BMP-5 | - | - | - | - | - | - | - | - | - | - |
| OP-1 | - | - | - | - | - | - | - | - | - | - |
| Vgr-1 | - | - | - | - | - | - | - | - | - | - |
| Vg-1 | - | - | - | - | - | - | - | - | - | - |
| GDF-1 | - | - | - | - | - | - | - | - | - | - |
| GDF-9 | - | - | - | - | - | - | - | - | - | - |
| GDF-3 | - | - | - | - | - | - | - | - | - | - |

FIG. 4b

```
  1 AAGGGGTTCATGGCAAATTACTGCCATGGAGAGTGTCCCTTCTCTCACTGACCATCTCTC   60
    K  G  F  M  A  N  Y  C  H  G  E  C  P  F  S  L  T  I  S  L
 61 AACAGCTCCAATTATGCTTTCATGCAAGCCCTGATGCATGCCGTTGACCCAGAGATCCCC  120
    N  S  S  N  Y  A  F  M  Q  A  L  M  H  A  V  D  P  E  I  P
121 CAGGCTGTGTGTATCCCCACCAAGCTGTCTCCCATTCCATGCTCTACCAGGACAATAAT  180
    Q  A  V  C  I  P  T  K  L  S  P  I  S  M  L  Y  Q  D  N  N
181 GACAATGTCATTCTACGACAT 201
    D  N  V  I  L  R  H
```

FIG.5

```
                        SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: SJL120

(ix) FEATURE:
         (A) NAME/KEY: CDS
         (B) LOCATION: 1..41
         (D) OTHER INFORMATION: /note= "Where "R" Occurs, R =
             Adenine or Guanine; N = Inosine; Y = Thymine or
             Cytosine; M = Adenine or Cytosine."

(xi) SEQUENCE DESCRIPTION: SEQ ID NO:1:
```

```
CCGGAATTCG ARGTNGGNTG GCAYMGNTGG GTNATNGCNC C                    41
```

(2) INFORMATION FOR SEQ ID NO:2:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: SJL121

(ix) FEATURE:
        (A) NAME/KEY: CDS
        (B) LOCATION: 1..42
        (D) OTHER INFORMATION: /note= "WHERE "R" OCCURS, R =
            GUANINE OR ADENINE; WHERE "N" OCCURS, N = INOSINE;
            WHERE "Y" OCCURS, Y = THYMINE OR CYTOSINE."

(xi) SEQUENCE DESCRIPTION: SEQ ID NO:2:

```
CCGGAATTCR CANCCRCAYT CRTCNACNAC CATRTCYTCR TA                   42
```

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: SJL120

(ix) FEATURE:
        (A) NAME/KEY: Peptide
        (B) LOCATION: 1..11
        (D) OTHER INFORMATION: /note= "Where "Arg" Occurs, Arg =
            Arg or Ser; Where "Ile" occurs, Ile = Ile or Met."

(xi) SEQUENCE DESCRIPTION: SEQ ID NO:3:

```
Glu Val Gly Trp His Arg Trp Val Ile Ala Pro
1               5                   10
```

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: SJL121

(ix) FEATURE:
        (A) NAME/KEY: Peptide
        (B) LOCATION: 1..11

(xi) SEQUENCE DESCRIPTION: SEQ ID NO:4:

```
Tyr Glu Asp Met Val Val Asp Glu Cys Gly Cys
1               5                   10
```

(2) INFORMATION FOR SEQ ID NO:5:

-continued

```
    (i) SEQUENCE CHARACTERISTICS:
        (A) LENGTH: 1280 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: GDF-3

(ix) FEATURE:
        (A) NAME/KEY: CDS
        (B) LOCATION: 122..1219

(xi) SEQUENCE DESCRIPTION: SEQ ID NO:5:

TGAGGGGCTG AGAAGAGAGC AATTCACACT TGATTAGCTC CCAGGCTCCT GAATTGAGCA      60

GAGGAGGCTA GACCGCTGAG CTGCGCACCC CAGAGGCTGC TCTACCCTGG CTCAGACGAC     120

C ATG CAG CCT TAT CAA CGG CTT CTG GCG CTT GGC TTC CTT CTG TTA        166
  Met Gln Pro Tyr Gln Arg Leu Leu Ala Leu Gly Phe Leu Leu Leu
   1               5                  10                  15

ACC CTG CCC TGG GGC CAG ACA TCC GAG TTT CAA GAC TCT GAC CTT TTG      214
Thr Leu Pro Trp Gly Gln Thr Ser Glu Phe Gln Asp Ser Asp Leu Leu
                 20                  25                  30

CAG TTT CTG GGA TTA GAG AAA GCG CCT TCA CCT CAC AGG TTC CAA CCT      262
Gln Phe Leu Gly Leu Glu Lys Ala Pro Ser Pro His Arg Phe Gln Pro
             35                  40                  45

GTG CCT CGC GTC TTA AGG AAA ATC ATC CGG GCT CGA GAA GCC GCT GCA      310
Val Pro Arg Val Leu Arg Lys Ile Ile Arg Ala Arg Glu Ala Ala Ala
         50                  55                  60

GCC AGT GGG GCC TCG CAG GAC TTA TGC TAC GTG AAG GAG CTG GGT GTT      358
Ala Ser Gly Ala Ser Gln Asp Leu Cys Tyr Val Lys Glu Leu Gly Val
     65                  70                  75

CGT GGG AAC CTG CTT CAG CTT CTC CCA GAC CAG GGT TTT TTC CTT AAT      406
Arg Gly Asn Leu Leu Gln Leu Leu Pro Asp Gln Gly Phe Phe Leu Asn
 80                  85                  90                  95

ACA CAG AAA CCT TTC CAA GAT GGC TCC TGT CTC CAG AAG GTC CTC TAT      454
Thr Gln Lys Pro Phe Gln Asp Gly Ser Cys Leu Gln Lys Val Leu Tyr
                100                 105                 110

TTT AAC TTG TCT GCC ATC AAA GAA AAG GCA AAG TTG ACC ATG GCC CAG      502
Phe Asn Leu Ser Ala Ile Lys Glu Lys Ala Lys Leu Thr Met Ala Gln
            115                 120                 125

CTG ACT CTA GAC TTG GGG CCC AGG TCC TAC TAT AAC CTG CGA CCA GAG      550
Leu Thr Leu Asp Leu Gly Pro Arg Ser Tyr Tyr Asn Leu Arg Pro Glu
        130                 135                 140

CTG GTG GTT GCT CTG TCT GTG GTT CAG GAC CGG GGC GTG TGG GGG CGA      598
Leu Val Val Ala Leu Ser Val Val Gln Asp Arg Gly Val Trp Gly Arg
    145                 150                 155

TCC CAC CCT AAG GTG GGC AGA TTG CTT TTT CTG CGG TCT GTC CCT GGG      646
Ser His Pro Lys Val Gly Arg Leu Leu Phe Leu Arg Ser Val Pro Gly
160                 165                 170                 175

CCT CAA GGT CAG CTC CAG TTC AAC CTG CAG GGT GCG CTT AAG GAT TGG      694
Pro Gln Gly Gln Leu Gln Phe Asn Leu Gln Gly Ala Leu Lys Asp Trp
                180                 185                 190

AGC AGC AAC CGA CTG AAG AAT TTG GAC TTA CAC TTA GAG ATT TTG GTC      742
Ser Ser Asn Arg Leu Lys Asn Leu Asp Leu His Leu Glu Ile Leu Val
            195                 200                 205

AAA GAG GAC AGA TAC TCC AGG GTA ACT GTC CAG CCC GAG AAC CCC TGT      790
Lys Glu Asp Arg Tyr Ser Arg Val Thr Val Gln Pro Glu Asn Pro Cys
        210                 215                 220

GAC CCG CTG CTC CGC TCT CTA CAT GCC TCG CTG CTG GTG GTA ACC CTC      838
Asp Pro Leu Leu Arg Ser Leu His Ala Ser Leu Leu Val Val Thr Leu
```

```
        225                 230                 235
AAT CCT AAA CAC TGT CAT CCT TCT TCC AGA AAA AGG AGG GCG GCC ATC          886
Asn Pro Lys His Cys His Pro Ser Ser Arg Lys Arg Arg Ala Ala Ile
240                 245                 250                 255

TCT GTC CCC AAG GGT TTC TGT AGG AAC TTC TGC CAC CGT CAT CAG CTG          934
Ser Val Pro Lys Gly Phe Cys Arg Asn Phe Cys His Arg His Gln Leu
                260                 265                 270

TTC ATC AAC TTC CAG GAC CTG GGT TGG CAC AAG TGG GTC ATC GCC CCT          982
Phe Ile Asn Phe Gln Asp Leu Gly Trp His Lys Trp Val Ile Ala Pro
            275                 280                 285

AAG GGG TTC ATG GCA AAT TAC TGT CAT GGA GAG TGC CCC TTC TCA ATG         1030
Lys Gly Phe Met Ala Asn Tyr Cys His Gly Glu Cys Pro Phe Ser Met
        290                 295                 300

ACC ACG TAT TTA AAT AGT TCC AAT TAT GCT TTC ATG CAG GCT CTG ATG         1078
Thr Thr Tyr Leu Asn Ser Ser Asn Tyr Ala Phe Met Gln Ala Leu Met
    305                 310                 315

CAT ATG GCT GAC CCC AAG GTC CCC AAG GCT GTC TGT GTC CCC ACC AAG         1126
His Met Ala Asp Pro Lys Val Pro Lys Ala Val Cys Val Pro Thr Lys
320                 325                 330                 335

CTC TCG CCC ATC TCC ATG CTC TAT CAG GAT AGT GAT AAG AAC GTC ATT         1174
Leu Ser Pro Ile Ser Met Leu Tyr Gln Asp Ser Asp Lys Asn Val Ile
                340                 345                 350

CTC CGA CAT TAT GAA GAC ATG GTA GTC GAT GAG TGT GGG TGT GGG             1219
Leu Arg His Tyr Glu Asp Met Val Val Asp Glu Cys Gly Cys Gly
            355                 360                 365

TAGTCTCGGG ACTAGGCTAG GAGTGTGCTT AGGGTAAATC CTTTAATAAA ACTACCACCC       1279

C                                                                       1280

(2) INFORMATION FOR SEQ ID NO:6:

(i) SEQUENCE CHARACTERISTICS:
        (A) LENGTH: 366 amino acids
        (B) TYPE: amino acid
        (D) TOPOLOGY: linear (ii) MOLECULE TYPE: protein (xi) SEQUENCE DESCRIPTION: SEQ ID NO:6:

Met Gln Pro Tyr Gln Arg Leu Leu Ala Leu Gly Phe Leu Leu Leu Thr
 1               5                  10                  15

Leu Pro Trp Gly Gln Thr Ser Glu Phe Gln Asp Ser Asp Leu Leu Gln
            20                  25                  30

Phe Leu Gly Leu Glu Lys Ala Pro Ser Pro His Arg Phe Gln Pro Val
        35                  40                  45

Pro Arg Val Leu Arg Lys Ile Ile Arg Ala Arg Glu Ala Ala Ala Ala
    50                  55                  60

Ser Gly Ala Ser Gln Asp Leu Cys Tyr Val Lys Glu Leu Gly Val Arg
65                  70                  75                  80

Gly Asn Leu Leu Gln Leu Leu Pro Asp Gln Gly Phe Leu Asn Thr
                85                  90                  95

Gln Lys Pro Phe Gln Asp Gly Ser Cys Leu Gln Lys Val Leu Tyr Phe
            100                 105                 110

Asn Leu Ser Ala Ile Lys Glu Lys Ala Lys Leu Thr Met Ala Gln Leu
        115                 120                 125

Thr Leu Asp Leu Gly Pro Arg Ser Tyr Tyr Asn Leu Arg Pro Glu Leu
    130                 135                 140

Val Val Ala Leu Ser Val Val Gln Asp Arg Gly Val Trp Gly Arg Ser
145                 150                 155                 160
```

```
His Pro Lys Val Gly Arg Leu Leu Phe Leu Arg Ser Val Pro Gly Pro
            165                 170                 175

Gln Gly Gln Leu Gln Phe Asn Leu Gln Gly Ala Leu Lys Asp Trp Ser
            180                 185                 190

Ser Asn Arg Leu Lys Asn Leu Asp Leu His Leu Glu Ile Leu Val Lys
            195                 200                 205

Glu Asp Arg Tyr Ser Arg Val Thr Val Gln Pro Glu Asn Pro Cys Asp
            210                 215                 220

Pro Leu Leu Arg Ser Leu His Ala Ser Leu Leu Val Val Thr Leu Asn
225                 230                 235                 240

Pro Lys His Cys His Pro Ser Ser Arg Lys Arg Arg Ala Ala Ile Ser
            245                 250                 255

Val Pro Lys Gly Phe Cys Arg Asn Phe Cys His Arg His Gln Leu Phe
            260                 265                 270

Ile Asn Phe Gln Asp Leu Gly Trp His Lys Trp Val Ile Ala Pro Lys
            275                 280                 285

Gly Phe Met Ala Asn Tyr Cys His Gly Glu Cys Pro Phe Ser Met Thr
            290                 295                 300

Thr Tyr Leu Asn Ser Ser Asn Tyr Ala Phe Met Gln Ala Leu Met His
305                 310                 315                 320

Met Ala Asp Pro Lys Val Pro Lys Ala Val Cys Val Pro Thr Lys Leu
            325                 330                 335

Ser Pro Ile Ser Met Leu Tyr Gln Asp Ser Asp Lys Asn Val Ile Leu
            340                 345                 350

Arg His Tyr Glu Asp Met Val Val Asp Glu Cys Gly Cys Gly
            355                 360                 365

(2) INFORMATION FOR SEQ ID NO:7:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: GDF-3

(ix) FEATURE:
        (A) NAME/KEY: Protein
        (B) LOCATION: 1..117

(xi) SEQUENCE DESCRIPTION: SEQ ID NO:7:

Lys Arg Arg Ala Ala Ile Ser Val Pro Lys Gly Phe Cys Arg Asn Phe
1               5                   10                  15

Cys His Arg His Gln Leu Phe Ile Asn Phe Gln Asp Leu Gly Trp His
            20                  25                  30

Lys Trp Val Ile Ala Pro Lys Gly Phe Met Ala Asn Tyr Cys His Gly
            35                  40                  45

Glu Cys Pro Phe Ser Met Thr Thr Tyr Leu Asn Ser Ser Asn Tyr Ala
        50                  55                  60

Phe Met Gln Ala Leu Met His Met Ala Asp Pro Lys Val Pro Lys Ala
65                  70                  75                  80

Val Cys Val Pro Thr Lys Leu Ser Pro Ile Ser Met Leu Tyr Gln Asp
            85                  90                  95

Ser Asp Lys Asn Val Ile Leu Arg His Tyr Glu Asp Met Val Val Asp
```

```
                100               105               110
Glu Cys Gly Cys Gly
            115
```

(2) INFORMATION FOR SEQ ID NO:8:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: GDF-9

(ix) FEATURE:
        (A) NAME/KEY: Protein
        (B) LOCATION: 1..118

(xi) SEQUENCE DESCRIPTION: SEQ ID NO:8:

```
Phe Asn Leu Ser Glu Tyr Phe Lys Gln Phe Leu Phe Pro Gln Asn Glu
1               5                   10                  15

Cys Glu Leu His Asp Phe Arg Leu Ser Phe Ser Gln Leu Lys Trp Asp
            20                  25                  30

Asn Trp Ile Val Ala Pro His Arg Tyr Asn Pro Arg Tyr Cys Lys Gly
        35                  40                  45

Asp Cys Pro Arg Ala Val Arg His Arg Tyr Gly Ser Pro Val His Thr
    50                  55                  60

Met Val Gln Asn Ile Ile Tyr Glu Lys Leu Asp Pro Ser Val Pro Arg
65                  70                  75                  80

Pro Ser Cys Val Pro Gly Lys Tyr Ser Pro Leu Ser Val Leu Thr Ile
            85                  90                  95

Glu Pro Asp Gly Ser Ile Ala Tyr Lys Glu Tyr Glu Asp Met Ile Ala
                100                 105                 110

Thr Arg Cys Thr Cys Arg
            115
```

(2) INFORMATION FOR SEQ ID NO:9:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: GDF-1

(ix) FEATURE:
        (A) NAME/KEY: Protein
        (B) LOCATION: 1..122

(xi) SEQUENCE DESCRIPTION: SEQ ID NO:9:

```
Pro Arg Arg Asp Ala Glu Pro Val Leu Gly Gly Pro Gly Gly Ala
1               5                   10                  15

Cys Arg Ala Arg Arg Leu Tyr Val Ser Phe Arg Glu Val Gly Trp His
            20                  25                  30

Arg Trp Val Ile Ala Pro Arg Gly Phe Leu Ala Asn Tyr Cys Gln Gly
        35                  40                  45

Gln Cys Ala Leu Pro Val Ala Leu Ser Gly Ser Gly Gly Pro Pro Ala
```

```
              50                  55                  60
Leu Asn His Ala Val Leu Arg Ala Leu Met His Ala Ala Pro Gly
 65                  70                  75                  80

Ala Ala Asp Leu Pro Cys Cys Val Pro Ala Arg Leu Ser Pro Ile Ser
                 85                  90                  95

Val Leu Phe Phe Asp Asn Ser Asp Asn Val Val Leu Arg Gln Tyr Glu
                100                 105                 110

Asp Met Val Val Asp Glu Cys Gly Cys Arg
                115                 120
```

(2) INFORMATION FOR SEQ ID NO:10:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Vg-1

(ix) FEATURE:
        (A) NAME/KEY: Protein
        (B) LOCATION: 1..118

(xi) SEQUENCE DESCRIPTION: SEQ ID NO:10:

```
Arg Arg Lys Arg Ser Tyr Ser Lys Leu Pro Phe Thr Ala Ser Asn Ile
 1               5                  10                  15

Cys Lys Lys Arg His Leu Tyr Val Glu Phe Lys Asp Val Gly Trp Gln
                 20                  25                  30

Asn Trp Val Ile Ala Pro Gln Gly Tyr Met Ala Asn Tyr Cys Tyr Gly
                 35                  40                  45

Glu Cys Pro Tyr Pro Leu Thr Glu Ile Leu Asn Gly Ser Asn His Ala
 50                  55                  60

Ile Leu Gln Thr Leu Val His Ser Ile Glu Pro Glu Asp Ile Pro Leu
 65                  70                  75                  80

Pro Cys Cys Val Pro Thr Lys Met Ser Pro Ile Ser Met Leu Phe Tyr
                 85                  90                  95

Asp Asn Asn Asp Asn Val Val Leu Arg His Tyr Glu Asn Met Ala Val
                100                 105                 110

Asp Glu Cys Gly Cys Arg
                115
```

(2) INFORMATION FOR SEQ ID NO:11:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Vgr-1

(ix) FEATURE:
        (A) NAME/KEY: Protein
        (B) LOCATION: 1..118

(xi) SEQUENCE DESCRIPTION: SEQ ID NO:11:

Arg Val Ser Ser Ala Ser Asp Tyr Asn Ser Ser Glu Leu Lys Thr Ala

```
1               5                   10                  15
Cys Arg Lys His Glu Leu Tyr Val Ser Val Gln Asp Leu Gly Trp Gln
            20                  25                  30

Asp Trp Ile Ile Ala Pro Lys Gly Tyr Ala Ala Asn Tyr Cys Asp Gly
            35              40                  45

Glu Cys Ser Phe Pro Leu Asn Ala His Met Asn Ala Thr Asn His Ala
    50                  55                  60

Ile Val Gln Thr Leu Val His Leu Met Asn Pro Glu Tyr Val Pro Lys
65              70                  75                      80

Pro Cys Cys Ala Pro Thr Lys Leu Asn Ala Ile Ser Val Leu Tyr Phe
                85                  90                  95

Asp Asp Asn Ser Asn Val Ile Leu Lys Lys Tyr Arg Asn Met Val Val
            100                 105                 110

Arg Ala Cys Gly Cys His
            115

(2) INFORMATION FOR SEQ ID NO:12:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: OP-1

(ix) FEATURE:
        (A) NAME/KEY: Protein
        (B) LOCATION: 1..118

(xi) SEQUENCE DESCRIPTION: SEQ ID NO:12:

Arg Met Ala Asn Val Ala Glu Asn Ser Ser Ser Asp Gln Arg Gln Ala
1               5                   10                  15

Cys Lys Lys His Glu Leu Tyr Val Ser Phe Arg Asp Leu Gly Trp Gln
            20                  25                  30

Asp Trp Ile Ile Ala Pro Glu Gly Tyr Ala Ala Tyr Tyr Cys Glu Gly
            35              40                  45

Glu Cys Ala Phe Pro Leu Asn Ser Tyr Met Asn Ala Thr Asn His Ala
    50                  55                  60

Ile Val Gln Thr Leu Val His Phe Ile Asn Pro Glu Thr Val Pro Lys
65              70                  75                      80

Pro Cys Cys Ala Pro Thr Gln Leu Asn Ala Ile Ser Val Leu Tyr Phe
                85                  90                  95

Asp Asp Ser Ser Asn Val Ile Leu Lys Lys Tyr Arg Asn Met Val Val
            100                 105                 110

Arg Ala Cys Gly Cys His
            115

(2) INFORMATION FOR SEQ ID NO:13:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
```

(B) CLONE: BMP-5

(ix) FEATURE:
         (A) NAME/KEY: Protein
         (B) LOCATION: 1..118

(xi) SEQUENCE DESCRIPTION: SEQ ID NO:13:

Arg Met Ser Ser Val Gly Asp Tyr Asn Thr Ser Glu Gln Lys Gln Ala
1               5                   10                  15

Cys Lys Lys His Glu Leu Tyr Val Ser Phe Arg Asp Leu Gly Trp Gln
                20                  25                  30

Asp Trp Ile Ile Ala Pro Glu Gly Tyr Ala Ala Phe Tyr Cys Asp Gly
            35                  40                  45

Glu Cys Ser Phe Pro Leu Asn Ala His Met Asn Ala Thr Asn His Ala
    50                  55                  60

Ile Val Gln Thr Leu Val His Leu Met Phe Pro Asp His Val Pro Lys
65              70                  75                      80

Pro Cys Cys Ala Pro Thr Lys Leu Asn Ala Ile Ser Val Leu Tyr Phe
                85                  90                  95

Asp Asp Ser Ser Asn Val Ile Leu Lys Lys Tyr Arg Asn Met Val Val
                100                 105                 110

Arg Ser Cys Gly Cys His
            115

(2) INFORMATION FOR SEQ ID NO:14:

(i) SEQUENCE CHARACTERISTICS:
         (A) LENGTH: 118 amino acids
         (B) TYPE: amino acid
         (C) STRANDEDNESS: single
         (D) TOPOLOGY: linear (ii) MOLECULE TYPE: protein (vii) IMMEDIATE SOURCE:
         (B) CLONE: 60A (ix) FEATURE:
         (A) NAME/KEY: Protein
         (B) LOCATION: 1..118

(xi) SEQUENCE DESCRIPTION: SEQ ID NO:14:

Ser Pro Asn Asn Val Pro Leu Leu Glu Pro Met Glu Ser Thr Arg Ser
1               5                   10                  15

Cys Gln Met Gln Thr Leu Tyr Ile Asp Phe Lys Asp Leu Gly Trp His
                20                  25                  30

Asp Trp Ile Ile Ala Pro Glu Gly Tyr Gly Ala Phe Tyr Cys Ser Gly
            35                  40                  45

Glu Cys Asn Phe Pro Leu Asn Ala His Met Asn Ala Thr Asn His Ala
    50                  55                  60

Ile Val Gln Thr Leu Val His Leu Leu Glu Pro Lys Lys Val Pro Lys
65              70                  75                      80

Pro Cys Cys Ala Pro Thr Arg Leu Gly Ala Leu Pro Val Leu Tyr His
                85                  90                  95

Leu Asn Asp Glu Asn Val Asn Leu Lys Lys Tyr Arg Asn Met Ile Val
                100                 105                 110

Lys Ser Cys Gly Cys His
            115

(2) INFORMATION FOR SEQ ID NO:15:

(i) SEQUENCE CHARACTERISTICS:
    (A) LENGTH: 117 amino acids
    (B) TYPE: amino acid
    (C) STRANDEDNESS: single
    (D) TOPOLOGY: linear (ii) MOLECULE TYPE: protein (vii) IMMEDIATE SOURCE:
    (B) CLONE: BMP-2

(ix) FEATURE:
    (A) NAME/KEY: Protein
    (B) LOCATION: 1..117

(xi) SEQUENCE DESCRIPTION: SEQ ID NO:15:

```
Glu Lys Arg Gln Ala Lys His Lys Gln Arg Lys Arg Leu Lys Ser Ser
1               5                   10                  15

Cys Lys Arg His Pro Leu Tyr Val Asp Phe Ser Asp Val Gly Trp Asn
                20                  25                  30

Asp Trp Ile Val Ala Pro Pro Gly Tyr His Ala Phe Tyr Cys His Gly
            35                  40                  45

Glu Cys Pro Phe Pro Leu Ala Asp His Leu Asn Ser Thr Asn His Ala
50                  55                  60

Ile Val Gln Thr Leu Val Asn Ser Val Asn Ser Lys Ile Pro Lys Ala
65                  70                  75                  80

Cys Cys Val Pro Thr Glu Leu Ser Ala Ile Ser Met Leu Tyr Leu Asp
                85                  90                  95

Glu Asn Glu Lys Val Val Leu Lys Asn Tyr Gln Asp Met Val Val Glu
                100                 105                 110

Gly Cys Gly Cys Arg
            115
```

(2) INFORMATION FOR SEQ ID NO:16:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: BMP-4

(ix) FEATURE:
        (A) NAME/KEY: Protein
        (B) LOCATION: 1..117

(xi) SEQUENCE DESCRIPTION: SEQ ID NO:16:

```
Arg Ser Pro Lys His His Ser Gln Arg Ala Arg Lys Lys Asn Lys Asn
1               5                   10                  15

Cys Arg Arg His Ser Leu Tyr Val Asp Phe Ser Asp Val Gly Trp Asn
                20                  25                  30

Asp Trp Ile Val Ala Pro Pro Gly Tyr Gln Ala Phe Tyr Cys His Gly
            35                  40                  45

Asp Cys Pro Phe Pro Leu Ala Asp His Leu Asn Ser Thr Asn His Ala
    50                  55                  60

Ile Val Gln Thr Leu Val Asn Ser Val Asn Ser Ser Ile Pro Lys Ala
65                  70                  75                  80

Cys Cys Val Pro Thr Glu Leu Ser Ala Ile Ser Met Leu Tyr Leu Asp
                85                  90                  95
```

-continued

```
Glu Tyr Asp Lys Val Val Leu Lys Asn Tyr Gln Glu Met Val Val Glu
            100                 105                 110
Gly Cys Gly Cys Arg
        115
```

(2) INFORMATION FOR SEQ ID NO:17:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: DPP (ix) FEATURE:
        (A) NAME/KEY: Protein
        (B) LOCATION: 1..118

(xi) SEQUENCE DESCRIPTION: SEQ ID NO:17:

```
Lys Arg His Ala Arg Arg Pro Thr Arg Arg Lys Asn His Asp Asp Thr
1               5                   10                  15
Cys Arg Arg His Ser Leu Tyr Val Asp Phe Ser Asp Val Gly Trp Asp
            20                  25                  30
Asp Trp Ile Val Ala Pro Leu Gly Tyr Asp Ala Tyr Tyr Cys His Gly
        35                  40                  45
Lys Cys Pro Phe Pro Leu Ala Asp His Phe Asn Ser Thr Asn His Ala
    50                  55                  60
Val Val Gln Thr Leu Val Asn Asn Met Asn Pro Gly Lys Val Pro Lys
65                  70                  75                  80
Ala Cys Cys Val Pro Thr Gln Leu Asp Ser Val Ala Met Leu Tyr Leu
                85                  90                  95
Asn Asp Gln Ser Thr Val Val Leu Lys Asn Tyr Gln Glu Met Thr Val
            100                 105                 110
Val Gly Cys Gly Cys Arg
        115
```

(2) INFORMATION FOR SEQ ID NO:18:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: BMP-3

(ix) FEATURE:
        (A) NAME/KEY: Protein
        (B) LOCATION: 1..119

(xi) SEQUENCE DESCRIPTION: SEQ ID NO:18:

```
Gln Thr Leu Lys Lys Ala Arg Arg Lys Gln Trp Ile Glu Pro Arg Asn
1               5                   10                  15
Cys Ala Arg Arg Tyr Leu Lys Val Asp Phe Ala Asp Ile Gly Trp Ser
            20                  25                  30
Glu Trp Ile Ile Ser Pro Lys Ser Phe Asp Ala Tyr Tyr Cys Ser Gly
        35                  40                  45
```

```
Ala Cys Gln Phe Pro Met Pro Lys Ser Leu Lys Pro Ser Asn His Ala
    50                  55                  60

Thr Ile Gln Ser Ile Val Arg Ala Val Gly Val Pro Gly Ile Pro
65                  70                  75                  80

Glu Pro Cys Cys Val Pro Glu Lys Met Ser Ser Leu Ser Ile Leu Phe
            85                  90                  95

Phe Asp Glu Asn Lys Asn Val Val Leu Lys Val Tyr Pro Asn Met Thr
                100                 105                 110

Val Glu Ser Cys Ala Cys Arg
        115

(2) INFORMATION FOR SEQ ID NO:19:

(i) SEQUENCE CHARACTERISTICS:
        (A) LENGTH: 115 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: MIS (ix) FEATURE:
        (A) NAME/KEY: Protein
        (B) LOCATION: 1..115

(xi) SEQUENCE DESCRIPTION: SEQ ID NO:19:

Pro Gly Arg Ala Gln Arg Ser Ala Gly Ala Thr Ala Ala Asp Gly Pro
1                   5                   10                  15

Cys Ala Leu Arg Glu Leu Ser Val Asp Leu Arg Ala Glu Arg Ser Val
                20                  25                  30

Leu Ile Pro Glu Thr Tyr Gln Ala Asn Asn Cys Gln Gly Val Cys Gly
            35                  40                  45

Trp Pro Gln Ser Asp Arg Asn Pro Arg Tyr Gly Asn His Val Val Leu
    50                  55                  60

Leu Leu Lys Met Gln Ala Arg Gly Ala Ala Leu Ala Arg Pro Pro Cys
65                  70                  75                  80

Cys Val Pro Thr Ala Tyr Ala Gly Lys Leu Leu Ile Ser Leu Ser Glu
            85                  90                  95

Glu Arg Ile Ser Ala His His Val Pro Asn Met Val Ala Thr Glu Cys
                100                 105                 110

Gly Cys Arg
        115

(2) INFORMATION FOR SEQ ID NO:20:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Inhibin alpha (ix) FEATURE:
        (A) NAME/KEY: Protein
        (B) LOCATION: 1..121

(xi) SEQUENCE DESCRIPTION: SEQ ID NO:20:
```

```
Leu Arg Leu Leu Gln Arg Pro Pro Glu Pro Ala Ala His Ala Asn
1               5                  10                 15

Cys His Arg Val Ala Leu Asn Ile Ser Phe Gln Glu Leu Gly Trp Glu
            20                  25                  30

Arg Trp Ile Val Tyr Pro Pro Ser Phe Ile Phe His Tyr Cys His Gly
            35                  40                  45

Gly Cys Gly Leu His Ile Pro Asn Leu Ser Leu Pro Val Pro Gly
    50                  55                  60

Ala Pro Pro Thr Pro Ala Gln Pro Tyr Ser Leu Leu Pro Gly Ala Gln
65                  70                  75                  80

Pro Cys Cys Ala Ala Leu Pro Gly Thr Met Arg Pro Leu His Val Arg
                85                  90                  95

Thr Thr Ser Asp Gly Gly Tyr Ser Phe Lys Tyr Glu Thr Val Pro Asn
            100                 105                 110

Leu Leu Thr Gln His Cys Ala Cys Ile
            115                 120
```

(2) INFORMATION FOR SEQ ID NO:21:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Inhibin beta A (ix) FEATURE:
        (A) NAME/KEY: Protein
        (B) LOCATION: 1..121

(xi) SEQUENCE DESCRIPTION: SEQ ID NO:21:

```
Arg Arg Arg Arg Arg Gly Leu Glu Cys Asp Gly Lys Val Asn Ile Cys
1               5                  10                  15

Cys Lys Lys Gln Phe Phe Val Ser Phe Lys Asp Ile Gly Trp Asn Asp
            20                  25                  30

Trp Ile Ile Ala Pro Ser Gly Tyr His Ala Asn Tyr Cys Glu Gly Glu
            35                  40                  45

Cys Pro Ser His Ile Ala Gly Thr Ser Gly Ser Ser Leu Ser Phe His
    50                  55                  60

Ser Thr Val Ile Asn His Tyr Arg Met Arg Gly His Ser Pro Phe Ala
65                  70                  75                  80

Asn Leu Lys Ser Cys Cys Val Pro Thr Lys Leu Arg Pro Met Ser Met
                85                  90                  95

Leu Tyr Tyr Asp Asp Gly Gln Asn Ile Ile Lys Lys Asp Ile Gln Asn
            100                 105                 110

Met Ile Val Glu Glu Cys Gly Cys Ser
            115                 120
```

(2) INFORMATION FOR SEQ ID NO:22:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein

```
        (vii) IMMEDIATE SOURCE:
              (B) CLONE: Inhibin beta B (ix) FEATURE:
              (A) NAME/KEY: Protein
              (B) LOCATION: 1..120

(xi) SEQUENCE DESCRIPTION: SEQ ID NO:22:

Arg Ile Arg Lys Arg Gly Leu Glu Cys Asp Gly Arg Thr Asn Leu Cys
1               5                  10                  15

Cys Arg Gln Gln Phe Phe Ile Asp Phe Arg Leu Ile Gly Trp Asn Asp
            20                  25                  30

Trp Ile Ile Ala Pro Thr Gly Tyr Tyr Gly Asn Tyr Cys Glu Gly Ser
        35                  40                  45

Cys Pro Ala Tyr Leu Ala Gly Val Pro Gly Ser Ala Ser Ser Phe His
    50                  55                  60

Thr Ala Val Val Asn Gln Tyr Arg Met Arg Gly Leu Asn Pro Gly Thr
65                  70                  75                  80

Val Asn Ser Cys Cys Ile Pro Thr Lys Leu Ser Thr Met Ser Met Leu
                85                  90                  95

Tyr Phe Asp Asp Glu Tyr Asn Ile Val Lys Arg Asp Val Pro Asn Met
            100                 105                 110

Ile Val Glu Glu Cys Gly Cys Ala
        115                 120

(2) INFORMATION FOR SEQ ID NO:23:

(i) SEQUENCE CHARACTERISTICS:
              (A) LENGTH: 114 amino acids
              (B) TYPE: amino acid
              (C) STRANDEDNESS: single
              (D) TOPOLOGY: linear (ii) MOLECULE TYPE: protein (vii) IMMEDIATE SOURCE:
              (B) CLONE: TGF-beta 1

(ix) FEATURE:
              (A) NAME/KEY: Protein
              (B) LOCATION: 1..114

(xi) SEQUENCE DESCRIPTION: SEQ ID NO:23:

Arg Arg Ala Leu Asp Thr Asn Tyr Cys Phe Ser Ser Thr Glu Lys Asn
1               5                  10                  15

Cys Cys Val Arg Gln Leu Tyr Ile Asp Phe Arg Lys Asp Leu Gly Trp
            20                  25                  30

Lys Trp Ile His Glu Pro Lys Gly Tyr His Ala Asn Phe Cys Leu Gly
        35                  40                  45

Pro Cys Pro Tyr Ile Trp Ser Leu Asp Thr Gln Tyr Ser Lys Val Leu
    50                  55                  60

Ala Leu Tyr Asn Gln His Asn Pro Gly Ala Ser Ala Ala Pro Cys Cys
65                  70                  75                  80

Val Pro Gln Ala Leu Glu Pro Leu Pro Ile Val Tyr Tyr Val Gly Arg
                85                  90                  95

Lys Pro Lys Val Glu Gln Leu Ser Asn Met Ile Val Arg Ser Cys Lys
            100                 105                 110

Cys Ser (2) INFORMATION FOR SEQ ID NO:24:
```

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TGF-beta 2

(ix) FEATURE:
        (A) NAME/KEY: Protein
        (B) LOCATION: 1..114

(xi) SEQUENCE DESCRIPTION: SEQ ID NO:24:

Lys Arg Ala Leu Asp Ala Ala Tyr Cys Phe Arg Asn Val Gln Asp Asn
1               5                  10                  15

Cys Cys Leu Arg Pro Leu Tyr Ile Asp Phe Lys Arg Asp Leu Gly Trp
            20                  25                  30

Lys Trp Ile His Glu Pro Lys Gly Tyr Asn Ala Asn Phe Cys Ala Gly
                35                  40                  45

Ala Cys Pro Tyr Leu Trp Ser Ser Asp Thr Gln His Ser Arg Val Leu
    50                  55                  60

Ser Leu Tyr Asn Thr Ile Asn Pro Glu Ala Ser Ala Ser Pro Cys Cys
65                  70                  75                  80

Val Ser Gln Asp Leu Glu Pro Leu Thr Ile Leu Tyr Tyr Ile Gly Lys
                85                  90                  95

Thr Pro Lys Ile Glu Gln Leu Ser Asn Met Ile Val Lys Ser Cys Lys
            100                 105                 110

Cys Ser (2) INFORMATION FOR SEQ ID NO:25:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TGF-beta 3

(ix) FEATURE:
        (A) NAME/KEY: Protein
        (B) LOCATION: 1..114

(xi) SEQUENCE DESCRIPTION: SEQ ID NO:25:

Lys Arg Ala Leu Asp Thr Asn Tyr Cys Phe Arg Asn Leu Glu Glu Asn
1               5                  10                  15

Cys Cys Val Arg Pro Leu Tyr Ile Asp Phe Arg Gln Asp Leu Gly Trp
            20                  25                  30

Lys Trp Val His Glu Pro Lys Gly Tyr Tyr Ala Asn Phe Cys Ser Gly
                35                  40                  45

Pro Cys Pro Tyr Leu Arg Ser Ala Asp Thr Thr His Ser Thr Val Leu
    50                  55                  60

Gly Leu Tyr Asn Thr Leu Asn Pro Glu Ala Ser Ala Ser Pro Cys Cys
65                  70                  75                  80

Val Pro Gln Asp Leu Glu Pro Leu Thr Ile Leu Tyr Tyr Val Gly Arg
                85                  90                  95

Thr Pro Lys Val Glu Gln Leu Ser Asn Met Val Val Lys Ser Cys Lys

```
                    100                 105                 110
Cys Ser (2) INFORMATION FOR SEQ ID NO:26:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TGF-beta 4

(ix) FEATURE:
        (A) NAME/KEY: Protein
        (B) LOCATION: 1..116

(xi) SEQUENCE DESCRIPTION: SEQ ID NO:26:

Arg Arg Asp Leu Asp Thr Asp Tyr Cys Phe Gly Pro Gly Thr Asp Glu
1               5                  10                  15

Lys Asn Cys Cys Val Arg Pro Leu Tyr Ile Asp Phe Arg Lys Asp Leu
                20                  25                  30

Gln Trp Lys Trp Ile His Glu Pro Lys Gly Tyr Met Ala Asn Phe Cys
            35                  40                  45

Met Gly Pro Cys Pro Tyr Ile Trp Ser Ala Asp Thr Gln Tyr Thr Lys
        50                  55                  60

Val Leu Ala Leu Tyr Asn Gln His Asn Pro Gly Ala Ser Ala Ala Pro
65                  70                  75                  80

Cys Cys Val Pro Gln Thr Leu Asp Pro Leu Pro Ile Ile Tyr Tyr Val
                85                  90                  95

Gly Arg Asn Val Arg Val Glu Gln Leu Ser Asn Met Val Val Arg Ala
                100                 105                 110

Cys Lys Cys Ser
        115

(2) INFORMATION FOR SEQ ID NO:27:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TGF-beta 5

(ix) FEATURE:
        (A) NAME/KEY: Protein
        (B) LOCATION: 1..114

(xi) SEQUENCE DESCRIPTION: SEQ ID NO:27:

Lys Arg Gly Val Gly Gln Glu Tyr Cys Phe Gly Asn Asn Gly Pro Asn
1               5                  10                  15

Cys Cys Val Lys Pro Leu Tyr Ile Asn Phe Arg Lys Asp Leu Gly Trp
                20                  25                  30

Lys Trp Ile His Glu Pro Lys Gly Tyr Glu Ala Asn Tyr Cys Leu Gly
            35                  40                  45

Asn Cys Pro Tyr Ile Trp Ser Met Asp Thr Gln Tyr Ser Lys Val Leu
        50                  55                  60
```

Ser Leu Tyr Asn Gln Asn Asn Pro Gly Ala Ser Ile Ser Pro Cys Cys
65                  70                  75                  80

Val Pro Asp Val Leu Glu Pro Leu Pro Ile Ile Tyr Tyr Val Gly Arg
                85                  90                  95

Thr Ala Lys Val Glu Gln Leu Ser Asn Met Val Val Arg Ser Cys Asn
            100                 105                 110

Cys Ser (2) INFORMATION FOR SEQ ID NO:28:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: GDF-3

(ix) FEATURE:
        (A) NAME/KEY: CDS
        (B) LOCATION: 1..201

(xi) SEQUENCE DESCRIPTION: SEQ ID NO:28:

AAG GGG TTC ATG GCA AAT TAC TGC CAT GGA GAG TGT CCC TTC TCA CTG        48
Lys Gly Phe Met Ala Asn Tyr Cys His Gly Glu Cys Pro Phe Ser Leu
1               5                   10                  15

ACC ATC TCT CTC AAC AGC TCC AAT TAT GCT TTC ATG CAA GCC CTG ATG        96
Thr Ile Ser Leu Asn Ser Ser Asn Tyr Ala Phe Met Gln Ala Leu Met
            20                  25                  30

CAT GCC GTT GAC CCA GAG ATC CCC CAG GCT GTG TGT ATC CCC ACC AAG        144
His Ala Val Asp Pro Glu Ile Pro Gln Ala Val Cys Ile Pro Thr Lys
        35                  40                  45

CTG TCT CCC ATT TCC ATG CTC TAC CAG GAC AAT AAT GAC AAT GTC ATT        192
Leu Ser Pro Ile Ser Met Leu Tyr Gln Asp Asn Asn Asp Asn Val Ile
    50                  55                  60

CTA CGA CAT                                                            201
Leu Arg His
65

(2) INFORMATION FOR SEQ ID NO:29:

(i) SEQUENCE CHARACTERISTICS:
        (A) LENGTH: 67 amino acids
        (B) TYPE: amino acid
        (D) TOPOLOGY: linear (ii) MOLECULE TYPE: protein (xi) SEQUENCE DESCRIPTION: SEQ ID NO:29:

Lys Gly Phe Met Ala Asn Tyr Cys His Gly Glu Cys Pro Phe Ser Leu
1               5                   10                  15

Thr Ile Ser Leu Asn Ser Ser Asn Tyr Ala Phe Met Gln Ala Leu Met
            20                  25                  30

His Ala Val Asp Pro Glu Ile Pro Gln Ala Val Cys Ile Pro Thr Lys
        35                  40                  45

Leu Ser Pro Ile Ser Met Leu Tyr Gln Asp Asn Asn Asp Asn Val Ile
    50                  55                  60

Leu Arg His
65

GROWTH DIFFERENTIATION FACTOR-3

This is a divisional of U.S. application Ser. No. 08/481,377, filed Aug. 28, 1995, issued Sep. 15, 1998 as U.S. Pat. No. 5,808,007, which is a 371 of PCT/US94/00666, filed Jan. 12, 1994, which is a continuation-in-part of U.S. application Ser. No. 08/003,140, filed Jan. 12, 1993, now abandoned.

BACKGROUND OF THE INVENTION

1. Field of the Invention

The invention relates generally to growth factors and specifically to a new member of the transforming growth factor beta (TGF-β) superfamily, which is denoted, growth differentiation factor-3 (GDF-3).

2. Description of Related Art

The transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer, et al., *Nature,* 345:167, 1990). *Drosophila decapentaplegic* (DPP) gene product, which is required for dorsal-ventral axis formation and morphogenesis of the imaginal disks (Padgett, et al., *Nature,* 325:81–84, 1987), the Xenopus Vg-1 gene product, which localizes to the vegetal pole of eggs ((Weeks, et al., *Cell,* 51:861–867, 1987), the activins (Mason, et al., *Biochem, Biophys. Res. Commun.,* 135:957–964, 1986), which can induce the formation of mesoderm and anterior structures in Xenopus embryos (Thomsen, et al., *Cell,* 63:485, 1990), and the bone morphogenetic proteins (BMPs, osteogenin, OP-1) which can induce de novo cartilage and bone formation (Sampath, et al., *J. Biol. Chem.,* 265:13198, 1990). The TGF-βs can influence a variety of differentiation processes, including adipogenesis, myogenesis, chondrogenesis, hematopoiesis, and epithelial cell differentiation (for review, see Massague, *Cell* 49:437, 1987).

The proteins of the TGF-β family are initially synthesized as a large precursor protein which subsequently undergoes proteolytic cleavage at a cluster of basic residues approximately 110–140 amino acids from the C-terminus. The C-terminal regions of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species has been found to be biologically active, but for other family members, like the inhibins (Ling, et al., *Nature,* 321:779, 1986) and the TGF-βs (Cheifetz, et al., *Cell,* 48:409, 1987), heterodimers have also been detected, and these appear to have different biological properties than the respective homodimers.

Identification of new factors that are tissue-specific in their expression pattern will provide a greater understanding of that tissue's development and function.

SUMMARY OF THE INVENTION

The present invention provides a cell growth and differentiation factor, GDF-3, a polynucleotide sequence which encodes the factor, and antibodies which are immunoreactive with the factor. This factor appears to relate to various cell proliferative disorders, especially those involving those involving hematopoietic and adipose tissue, as well as disorders related to the function of the immune system.

Thus, in one embodiment, the invention provides a method for detecting a cell proliferative or immunologic disorder of bone marrow, spleen, thymus or fat origin and which is associated with GDF-3. In another embodiment, the invention provides a method of treating a cell proliferative or immunologic disorder associated with abnormal levels of expression of GDF-3, by suppressing or enhancing GDF-3 activity.

BRIEF DESCRIPTION OF THE DRAWINGS

FIGS. 2a–b show nucleotide (SEQ ID NO:5) and predicted amino acid sequence (SEQ ID NO:6) of GDF-3. Consensus N-glycosylation signals are denoted by plain boxes. The putatve tetrabasic processing sites are denoted by stippled boxes. The in-frame termination codons upstream of the putative initiating ATG and the consensus polyadenylation signals are underlined. The poly A tails are not shown. Numbers indicate nucleotide position relative to the 5' end.

FIGS. 3a–b show the alignment of the C-terminal sequences of GDF-3 with other members of the TGF-β family (SEQ ID NO:7–27). The conserved cysteine residues are shaded. Dashes denote gaps introduced in order to maximize alignment.

FIGS. 4a–b show amino acid homologies among the different members of the TGF-β superfamily. Numbers represent percent amino acid identities between each pair calculated from the first conserved cysteine to the C-terminus. Boxes represent homologies among highly-related members within particular subgroups.

FIG. 5 shows the partial nucleotide (SEQ ID NO:28) and predicted amino acid (SEQ ID NO:29) sequences of human GDF-3.

DETAILED DESCRIPTION OF THE INVENTION

Figure 1:
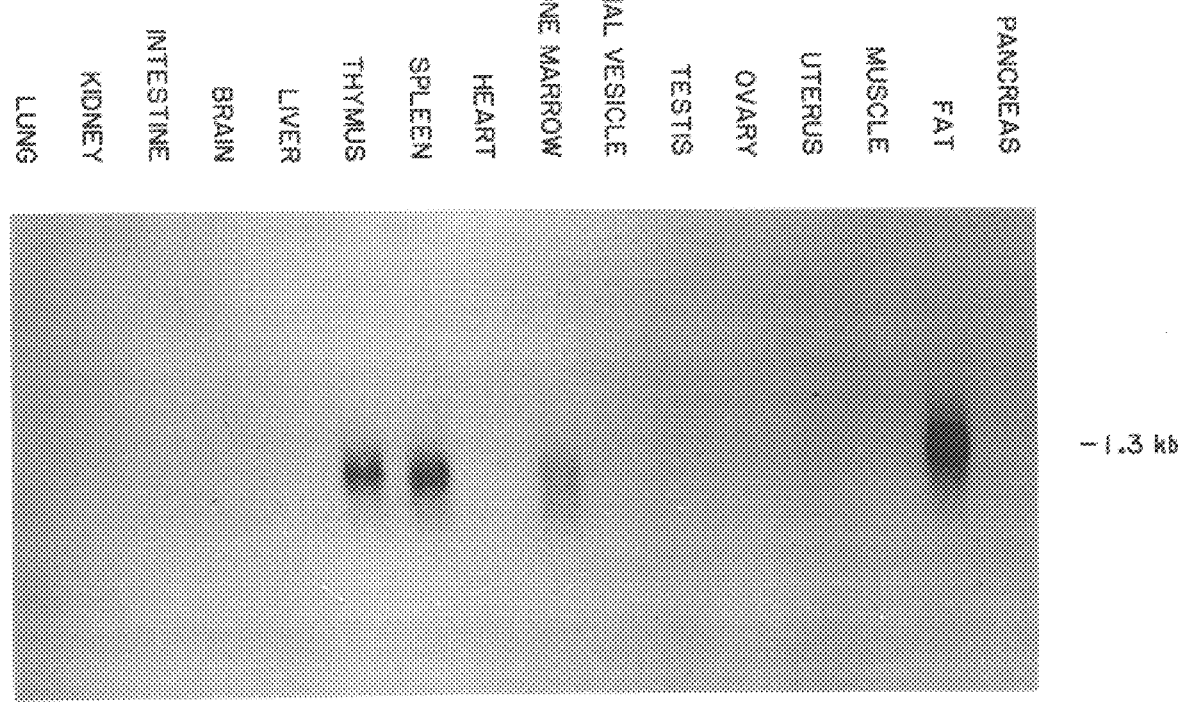
FIG. 1 shows expression of GDF-3 mRNA in adult tissues.

The present invention provides a growth and differentiation factor, GDF-3 and a polynucleotide sequence encoding GDF-3. GDF-3 is expressed primarily in the bone marrow, spleen, thymus and adipose tissue and may have multiple regulatory roles in animals. In one embodiment, the invention provides a method for detection of a cell proliferative or immunologic disorder of the bone marrow, spleen, thymus or adipose tissue which is associated with GDF-3 expression. In another embodiment, the invention provides a method for treating a cell proliferative or immunologic disorder associated with abnormal expression of GDF-3 by using an agent which suppresses or enhances GDF-3 activity.

The TGF-β superfamily consists of multifunctionally polypeptides that control proliferation, differentiation, and other functions in many cell types. Many of the peptides have regulatory, both positive and negative, effects on other peptide growth factors. The structural homology between the GDF-3 protein of this invention and the members of the TGF-β family, indicates that GDF-3 is a new member of the family of growth and differentiation factors. Based on the known activities of many of the other members, it can be expected that GDF-3 will also possess biological activities that will make it useful as a diagnostic and therapeutic reagent.

For example, TGF-β has been shown to have a wide range of immuno-regulatory activities, including potent suppressive effects on B and T cell proliferation and function (for review, see Palladino, et al., *Ann.N.Y.Acad.Sci.*, 593:181, 1990). GDF-3 may also have similar activities and, therefore, may be useful as an anti-inflammatory agent or as a treatment for disorders related to abnormal proliferation of lymphocytes. In addition, both TGF-β and activin have been postulated to play a role in hematopoiesis. Specifically, TGF-β has been shown to be an inhibitor of the growth of early hematopoietic progenitor cells (for review, see Moore, *Blood* 78:1, 1991); in this regard, GDF-3 may be useful for protecting hematopoietic stem cells during chemotherapy. In addition, activin has been shown to be expressed in the bone marrow and spleen (Shiozaki, et al., *Proc. Natl. Acad. Sci. USA*, 89:1553, 1992) and to be capable of inducing erythroid differentiation (Murata, et al., *Proc. Natl. Acad. Sci.USA*, 85:2434, 1988). GDF-3 may possess a similar activity and may be useful for the treatment of diseases like thalassemias or sickle cell anemia. TGF-β has also been shown to be a potent inhibitor of adipocyte differentiation in vitro (Ignotz and Massague, *Proc.Natl.Acad.Sci.,USA* 82:8530, 1985); in this regard, GDF-3 may be useful for the treatment of obesity or of disorders related to abnormal proliferation of adipocytes.

GDF-3 may also function as a growth stimulatory factor and therefore be useful for the survival of various cell populations in vitro. In particular, if GDF-3 plays a role in the stimulation of proliferation of hematopoietic stem cells, GDF-3 may have applications in chemotherapy, in bone marrow transplants or in the treatment of certain types of anemias. GDF-3 can be used to rapidly expand stem cell and progenitor cell populations in vitro, greatly reducing the amount of tissue required for transplantation. In addition, GDF-3 may be useful in maintaining stem cell populations prior to transplantation. Many other of the members of the TGF-β family are also important mediators of tissue repair. TGF-β has been shown to have marked effects on the formation of collagen and causes a striking angiogenic response in the newborn mouse (Roberts, et al., *Proc. Natl. Acad. Sci. USA*, 83:4167, 1986). GDF-3 may also have similar activities and may be useful in repair of tissue injury caused by trauma or burns for example.

The term "substantially pure" as used herein refers to GDF-3 which is substantially free of other proteins, lipids, carbohydrates or other materials with which it is naturally associated. One skilled in the art can purify GDF-3 using standard techniques for protein purification. The substantially pure polypeptide will yield a single major band on a non-reducing polyacrylamide gel. The purity of the GDF-3 polypeptide can also be determined by amino-terminal amino acid sequence analysis. GDF-3 polypeptide includes functional fragments of the polypeptide, as long as the activity of GDF-3 remains. Smaller peptides containing the biological activity of GDF-3 are included in the invention.

The invention provides polynucleotides encoding the GDF-3 protein. These polynucleotides include DNA, cDNA and RNA sequences which encode GDF-3. It is understood that all polynucleotides encoding all or a portion of GDF-3 are also included herein, as long as they encode a polypeptide with GDF-3 activity. Such polynucleotides include naturally occurring, synthetic, and intentionally manipulated polynucleotides. For example, GDF-3 polynucleotide may be subjected to site-directed mutagenesis. The polynucleotide sequence for GDF-3 also includes antisense sequences. The polynucleotides of the invention include sequences that are degenerate as a result of the genetic code. There are 20 natural amino acids, most of which are specified by more than one condon. Therefore, all degenerate nucleotide sequences are included in the invention as long as the amino acid sequence of GDF-3 polypeptide encoded by the nucleotide sequence is functionally unchanged.

Specifically disclosed herein is a cDNA sequence for GDF-3 which is 1280 base pairs in length and contains an open reading frame beginning with a methionine codon at nucleotide 122. The encoded polypeptide is 366 amino acids in length with a molecular weight of about 41.5 kD, as determined by nucleotide sequence analysis. Upstream of the putative initiating methionine is an in-frame termination codon beginning at nucleotide 77. The GDF-3 sequence contains a core of hydrophobic amino acids near the N-terminus, suggestive of a signal sequence for secretion. GDF-3 contains two potential N-glycosylation sites at asparagine residues 113 and 308 and a putative tetrabasic proteolytic processing site (RKRR) at amino acids 249–252. Cleavage at this site would generate a mature fragment of GDF-3 predicted to be 114 amino acids in length and have an unglycosylated molecular weight of about 13.0 kD, as determined by nucleotide sequence analysis. One skilled in the art can modify, or partially or completely remove, the glycosyl groups from the GDF-3 protein using standard techniques. Therefore the functional protein or fragments thereof of the invention includes glycosylated, partially glycosylated and unglycosylated species of GDF-3.

The C-terminal region of GDF-3 following the putative proteolytic processing site shows significant homology to the known members of the TGF-β superfamily. The GDF-3 sequence contains most of the residues that are highly conserved in other family members (see FIG. 3). However, the GDF-3 sequence contains an altered pattern of cysteine residues in this C-terminal region. In particular, GDF-3 lacks one of the seven cysteine residues that are conserved in all other family members; that is, at amino acid position 330, where all other family members contain a cysteine residue, the GDF-3 sequence contains a valine residue. In addition, GDF-3 contains an additional cysteine residue at position 262, ten amino acids following the predicted cleavage site.

Among the known mammalian TGF-β family members, GDF-3 is most homologous to Vgr-1 and BMP-2 (53% sequence identity). GDF-3 is slightly more homologous to Xenopus Vg-1 (57% sequence identity), but is unlikely to be the murine homolog of Vg-1 (for example, Vgr-1 and BMP-2 are as homologous to Vg-1 as GDF-3 is to Vg-1). However, GDF-3 does show homology to both GDF-1 and Vg-1 in the pro-region upstream of the putative tetrabasic processing site (28% and 29%, respectively); this degree of sequence relatedness is comparable to that seen in the pro-regions between TGF-β1 and TGF-β2 (33%; de Martin, et al., *EMBO J.*, 6:3673, 1987). GDF-3 is also similar to GDF-1 in the degree to which its sequence is diverged across species. As is the case for GDF-1, the sequence homology between murine and human GDF-3 appears to be only in the range of 80–85% amino acid identity.

Minor modifications of the recombinant GDF-3 primary amino acid sequence may result in proteins which have substantially equivalent activity as compared to the GDF-3 polypeptide described herein. Such modifications may be deliberate, as by site-directed mutagenesis, or may be spontaneous. All of the polypeptides produced by these modifications are included herein as long as the biological activity of GDF-3 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-3 biological activity.

The nucleotide sequence encoding the GDF-3 polypeptide of the invention includes the disclosed sequence and conservative variations thereof. Tne term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the GDF-3 polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

The development of specific DNA sequences encoding GDF-3 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for GDF-3 peptides having at least one epitope, using antibodies specific for GDF-3. Such antibodies can be either polyclonally or monoclonally derived and used to detect expression product indicative of the presence of GDF-3 cDNA.

DNA sequences encoding GDF-3 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF-3 polynucleotide sequences may be inserted into a recombinant expression vector. The term "recombinant expression vector" refers to a plasmid, virus or other vehicle known in the art that has been manipulated by insertion or incorporation of the GDF-3 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding GDF-3 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-3 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors,* Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with GDF-3 polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature,* 256:495, 1975). The term antibody as used in this invention is meant to include intact molecules as well as fragments thereof, such as Fab and $F(ab')_2$, which are capable of binding an epitopic determinant on GDF-3.

The term "cell-proliferative disorder" denotes malignant as well as non-malignant cell populations which often appear to differ from the surrounding tissue both morphologically and genotypically. The GDF-3 polynucleotide that is an antisense molecule is useful in treating malignancies of the various organ systems, particularly, for example, cells in the bone marrow, spleen, thymus or adipose tissue. Essentially, any disorder which is etiologically linked to altered expression of GDF-3 could be considered susceptible to treatment with a GDF-3 suppressing reagent. One such disorder of associated with bone marrow-derived cells is leukemia, for example. The term "immunologic disorder" refers to a disorder involving cells of the immune system, for example lymphocytes. Such immunologic disorders include disorders associated with the inflammatory process for example. The immunologic disorder is not limited to an immunologic cell proliferative disorder.

The invention provides a method for detecting a cell proliferative or immunologic disorder of the bone marrow, spleen, thymus or adipose tissue which comprises contacting an anti-GDF-3 antibody with a cell suspected of having a GDF-3 associated disorder and detecting binding to the antibody. The antibody reactive with GDF-3 is labeled with a compound which allows detection of binding to GDF-3. For purposes of the invention, an antibody specific for GDF-3 polypeptide may be used to detect the level of GDF-3 in biological fluids and tissues. Any specimen containing a detectable amount of antigen can be used. A preferred sample of this invention is tissue of bone marrow origin, specifically tissue containing hematopoietic stem or progenitor cells. The level of GDF-3 in the suspect cell can be compared with the level in a normal cell to determine whether the subject has a GDF-3-associated cell proliferative or immunologic disorder. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific anti-hapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used in vitro and in vivo to monitor the course of amelioration of a GDF-3-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-3-associated disease is effective. The term "ameliorate" denotes a lessening of the detrimental effect of the GDF-3-associated disease in the subject receiving therapy.

The present invention identifies a nucleotide sequence that can be expressed in an altered manner as compared to expression in a normal cell, therefore it is possible to design appropriate therapeutic or diagnostic techniques directed to this sequence. Thus, where a cell-proliferative or immunologic disorder is associated with the expression of GDF-3, nucleic acid sequences that interfere with GDF-3 expression at the translational level can be used. This approach utilizes, for example, antisense nucleic acid and ribozymes to block translation of a specific GDF-3 mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target GDF-3-producing cell. The use of antisense methods to inhibit the in vitro translation of genes is well known in the art (Marcus-Sakura, *Anal. Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type, ribozymes are preferable to tetrahymena-type ribozymes for inactivating a specific mRNA species and 18-based recognition sequences are preferable to shorter recognition sequences.

The present invention also provides gene therapy for the treatment of cell proliferative or immunologic disorders which are mediated by GDF-3 protein. Such therapy would achieve its therapeutic effect by introduction of the GDF-3 antisense polynucleotide into cells having the proliferative disorder. Delivery of antisense GDF-3 polynucleotide can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-3 sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the GDF-3 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-3 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of GDF-3 in the bone marrow, spleen, thymus and adipose tissue, there are a variety of applications using the polypeptide, polynucleotide and antibodies of the invention, related to these tissues. GDF-3 could play a role in regulation of the hematopoiesis and therefore could be useful in various transplantation procedures. In addition to applications for tissue transplantation, applications include treatment of cell proliferative and immunologic disorders.

The following examples are intended to illustrate but not limit the invention. While they are typical of those that might be used, other procedures known to those skilled in the art may alternatively be used.

EXAMPLE 1

Identification and Isolation of a Novel TGF-β Family Member

To identify a new member of the TGF-β superfamily, degenerate oligonucleotides were designed which corresponded to two conserved regions among the known family members: one region spanning the two tryptophan residues conserved in all family members except MIS and the other region spanning the invariant cysteine residues near the C-terminus. These primers were used for polymerase chain reactions on mouse genomic DNA followed by subcloning the PCR products using restriction sites placed at the 5' ends of the primers, picking individual *E. coli* colonies carrying these subcloned inserts, and using a combination of random sequencing and hybridization analysis to eliminate known members of the superfamily.

GDF-3 was identified from a mixture of PCR products obtained with the primers

SJL120: 5'-CCGGAATTCGA(A/G)GTIGGITGGCA(T/C)(A/C)GITGGGTIATIGCICC-3' (SEQ ID NO:1) and SJL121: 5'-CCGGAATTC(G/A)CAICC(G/A)CA(T/C)TC(G/A)TCIACIACCAT(G/A)TC(T/C)TC(G/A)TA-3' (SEQ ID NO:2).

PCR using these primers was carried out with 2 μg mouse genomic DNA at 94° C. for 1 min, 42° C. for 2 min, and 72° C. for 3.5 min for 40 cycles.

PCR products of approximately 280 bp were gel-purified, digested with Eco RI, gel-purified again, and subcloned in the Bluescript vector (Stratagene, San Diego, Calif.). Bacterial colonies carrying individual subclones were picked into 96 well microtiter plates, and multiple replicas were prepared by plating the cells onto nitrocellulose. The replicate filters were hybridized to probes representing known members of the family, and DNA was prepared from non-hybridizing colonies for sequence analysis.

The primer combination of SJL120 and SJL121, encoding the amino acid sequences EVGWH(R/S)WV(I/M)AP (SEQ ID NO:3) and YEDMVVDECGC (SEQ ID NO:4) respectively yielded one previously identified sequence GDF-1 and two novel sequences, one of which was designated GDF-3, among 80 subclones analyzed.

RNA isolation and Northern analysis were carried out as described previously (Lee, S. J., Mol. Endocrinol., 4:1034, 1990) except that hybridization was carried out in 5×SSPE, 10% dextran sulfate, 50% formamide, 1% SDS, 200 μg/ml salmon DNA and 0.1% each of bovine serum albumin, ficoll, and polyvinylpyrrolidone. An oligo dT-primed cDNA library was prepared from 2.5 μg of bone marrow poly A-selected RNA in the lambda ZAP II vector according to the instructions provided by Stratagene. The library was amplified once prior to screening. Filters were hybridized as described previously (Lee, S. J., Proc. Natl. Acad. Sci. USA., 88:4250–4254, 1991). DNA sequencing of both strands was carried out using the dideoxy chain termination method (Sanger, et al., Proc. Natl. Acad. Sci., USA, 74:5463–5467, 1977) and a combination of the S1 nuclease/exonuclease III strategy (Henikoff, S., Gene, 28:351–359, 1984) and synthetic oligonucleotide primers.

EXAMPLE 2

Expresssion Pattern and Sequence of GDF-3

To determine the expression pattern of GDF-3, RNA samples prepared from a variety of adult tissues were screened by Northern analysis. Five micrograms of twice polyA-selected RNA prepared from each tissue were electrophoresed on formaldehyde gels, blotted and probed with GDF-3. As shown in FIG. 1, the GDF-3 probe detected a 1.3 kb mRNA expressed in thymus, spleen, bone marrow and adipose tissue.

A bone marrow cDNA library consisting of $1.8 \times 10^6$ recombinant phage was constructed in lambda ZAP II and screened with a probe derived from the GDF-3 PCR product. The entire nucleotide sequence of the longest hybridizing clone is shown in FIG. 2. Consensus N-glycosylation signals are denoted by plain boxes. The putative tetrabasic processing sites are denoted by stippled boxes. The in-frame termination codons upstream of the putative initiating ATG and the consensus polyadenylation signals are underlined. The poly A tails are not shown. Numbers indicate nucleotide position relative to the 5' end. The 1280 bp sequence contains a long open reading frame beginning with a methionine codon at nucleotide 122 and potentially encoding a protein 366 amino acids in length with a molecular weight of 41.5 kD. Upstream of the putative initiating methionine is an in-frame termination codon beginning at nucieotide 77. The predicted GDF-3 amino acid sequence contains a hydrophobic N-terminal region, suggestive of a signal sequence for secretion, two potential N-linked glycosylation sites at asparagine residues 113 and 308, and a putative tetrabasic proteolytic processing site (RKRR) (in SEQ ID NO:6 and 29) at amino acids 249–252. Cleavage of the GDF-3 precursor at this site would generate a mature GDF-3 protein 114 amino acids in length with a predicted unglycosylated molecular weight of 13.0 kD.

Figure 3A:
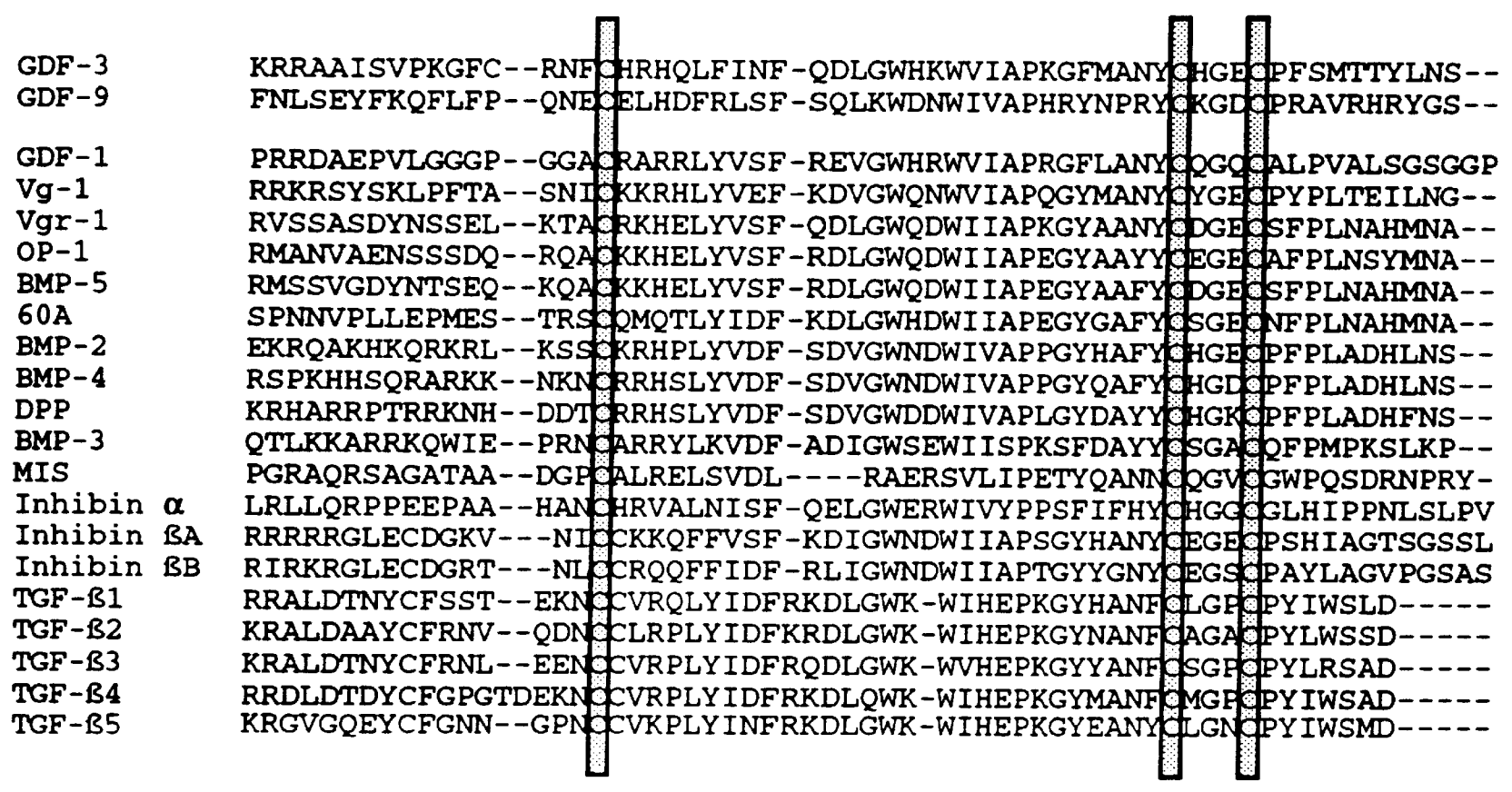
Figure 3B:
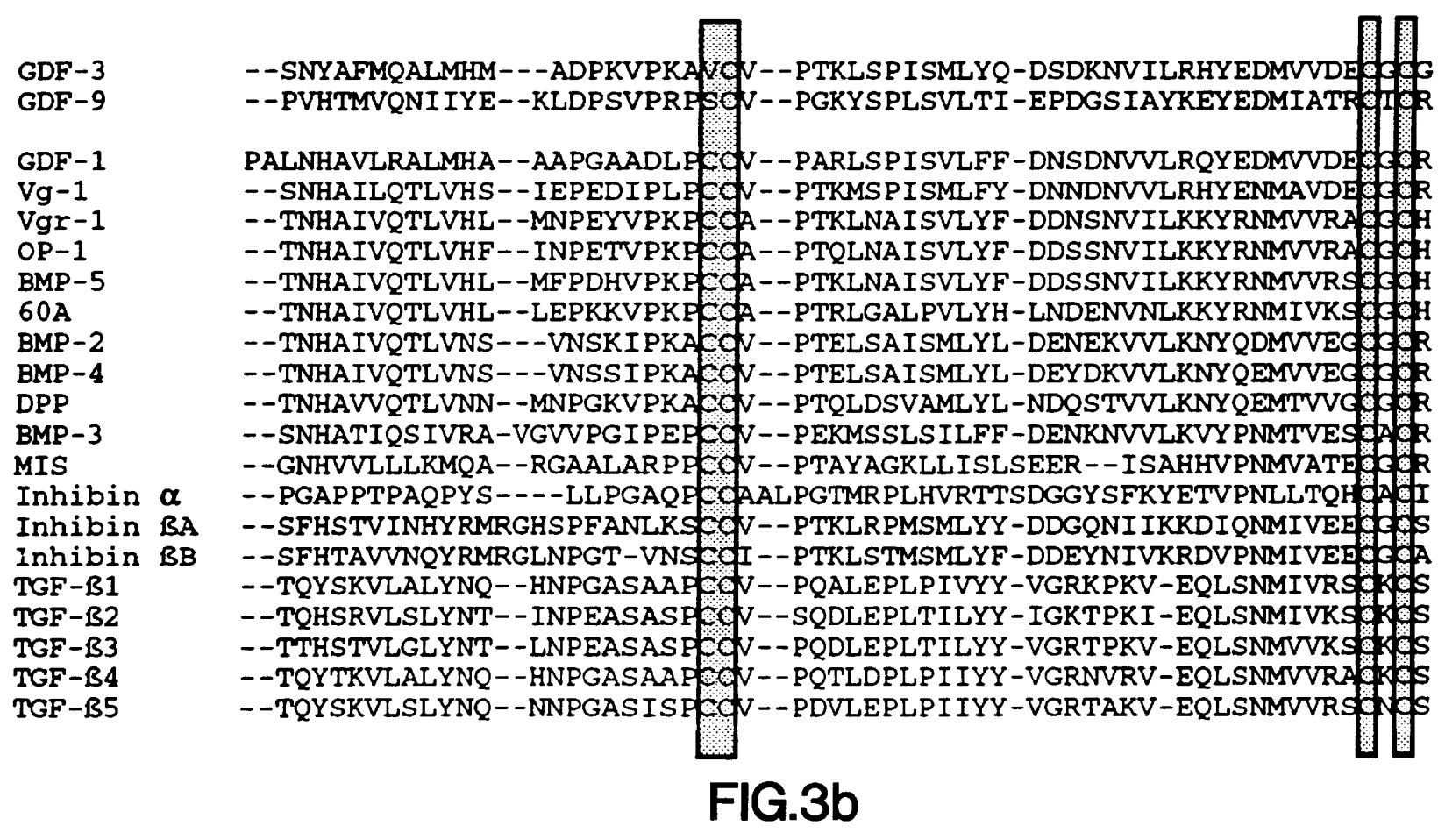

The C-terminal region of GDF-3 following the putative proteolytic processing site shows significant homology to the known members of the TGF-β superfamily (FIG. 3). FIG. 3 shows the alignment of the C-terminal sequences of GDF-3 with the corresponding regions of human GDF-1 (Lee, Proc. Natl. Acad. Sci. USA, 88:4250–4254,1991), Xenopus Vg-1 (Weeks, et al., Cell, 51:861–867, 1987), human Vgr-1 (Celeste, et al., Proc. Natl. Acad. Sci. USA, 87:9843–9847, 1990), human OP-1 (Ozkaynak, et al., EMBO J., 9:2085–2093, 1990), human BMP-5 (Celeste, et al., Proc. Natl. Acad. Sci. USA, 87:9843–9847, 1990), Drosophila 60A (Wharton, et al., Proc. Natl. Acad. Sci. USA, 88:9214–9218, 1991), human BMP-2 and 4 (Wozney, et al., Science, 242:1528–1534, 1988), Drosophila DPP (Padgett, et al., Nature, 325:81–84, 1987), human BMP-3 (Wozney, et al., Science, 242:1528–1534, 1988), human MIS (Cate, et al., Cell, 45:685–698, 1986), human inhibin alpha, βA, and βB (Mason, et al., Biochem, Biophys. Res. Commun., 135:957–964, 1986), human TGF-β1 (Derynck, et al., Nature, 316:701–705, 1985), human TGF-β2 (deMartin, et al., EMBO J., 6:3673–3677, 1987), human TGF-β3 (ten Dijke, et al., Proc. Natl. Acad. Sci. USA, 85:4715–4719, 1988), chicken TGF-β4 (Jakowlew, et al., Mol. Endocrinol., 2:1186–1195, 1988). and Xenopus TGF-β5 (Kondaiah, et al., J. Biol. Chem., 265:1089–1093, 1990). The conserved cysteine residues are shaded. Dashes denote gaps introduced in order to maximize the alignment.

FIG. 4 shows the amino acid homologies among the different members of the TGF-β superfamily. Numbers represent percent amino acid identities between each pair calculated from the first conserved cysteine to the C-terminus. Boxes represent homologies among highly-related members within particular subgroups.

GDF-3 lacks the fourth cysteine residue of the seven cysteines that are conserved in every other family member. This cysteine residue is known in the case of TGF-β2 to be the only cysteine involved in intermolecular disulfide bond formation in the mature dimer (Daopin, et al., Science, 257:369, 1992; Schlunegger and Grutter, Nature, 358:430, 1992). Therefore, GDF-3 may not form dimers or may form non-covalently-linked dimers in which the interaction between the subunits may be dynamic and subject to regulation. The GDF-3 sequence contains an additional cysteine residue four amino acids upstream of the first conserved cysteine. The only family members known to contain additional cysteine residues are the TGF-βs and inhibin βs, each of which contain two additional cysteine residues. In the case of TGF-β2, these additional cysteine residues are known to form an intramolecular disulfide bond (Daopin, supra). Because GDF-3 contains only a single additional cysteine residue, GDF-3 appears to be the only family member containing an unpaired cysteine. Alternatively, it is conceivable that GDF-3 does form a disulfide-linked dimer, either as a homodimer or as a heterodimer with another family member, and that this additional cysteine is involved in forming the intermolecular disulfide bond. Indeed, if the overall structure of GDF-3 is similar to that of TGF-β2, the location of this extra cysteine in the "thumb" of the "hand" (Daopin, supra) would be consistent with such a role.

EXAMPLE 3

Isolation of Human GDF-3

Figure 6:
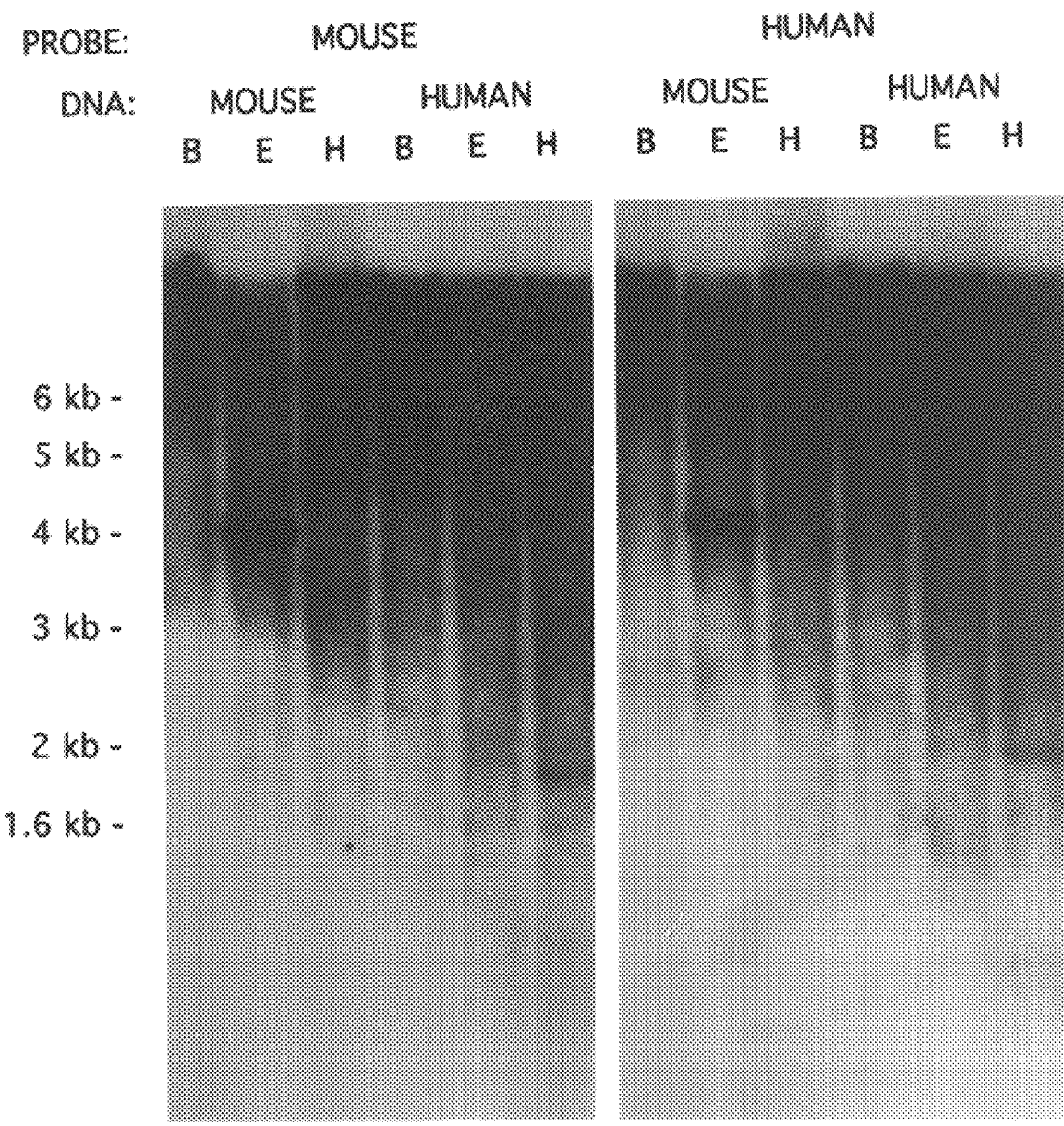
FIG. 6 shows Southern analysis of murine and human genomic DNA digested with Bam HI (B), Eco RI (E). or Hind III (H) and probed with either mouse or human GDF-3.

Using the same primer pair described in Example 1 (primers SJL 120 and 121) with human genomic DNA, a PCR product was obtained that showed significant homology (approximately 82% amino acid identity) to GDF-3 (FIG. 5). Southern analysis of mouse and human genomic DNA was carried out in 0.9 M sodium chloride, 50 mM sodium phosphate (pH 7.0), 10 mM EDTA, 10% dextran sulfate, 50% formamide, 1% SDS, 200 μg/ml salmon testis DNA and 0.1% each of bovine serum albumin, ficoll, and polyvinylpyrrolidone at 37° C. As shown in FIG. 6, the same pattern of hybridizing bands was obtained whether the probe was derived from the mouse GDF-3 sequence or from the highly related human sequence. Therefore the data show that the human sequence shown in FIG. 5 is the human GDF-3.

Although the invention has been described with reference to the presently preferred embodiment, it should be understood that various modifications can be made without departing from the spirit of the invention. Accordingly, the invention is limited only by the following claims.

SUMMARY OF SEQUENCES

SEQUENCE ID NO 1 is the nucleotide sequence of PCR primer, SJL120, for GDF-3.

SEQUENCE ID NO 2 is the nucleotide sequence of PCR primer, SJL121, for GDF-3.

SEQUENCE ID NO 3 is the amino acid sequence encoded by primer SJL120.

SEQUENCE ID NO 4 is the amino acid sequence encoded by primer SJL121.

SEQUENCE ID NO 5 is the nucleotide sequence and deduced amino acid sequence for murine GDF-3.

SEQUENCE ID NO 6 is the deduced amino acid sequence for murine GDF-3.

SEQUENCE ID NO 7 is the amino acid sequence of the C-terminal region of GDF-3.

SEQUENCE ID NO 8 is the amino acid sequence of the C-terminal region of GDF-9.

SEQUENCE ID NO 9 is the amino acid sequence of the C-terminal region of GDF-1.

SEQUENCE ID NO 10 is the amino acid sequence of the C-terminal region of Vg-1.

SEQUENCE ID NO 11 is the amino acid sequence of the C-terminal region of Vgr-1.

SEQUENCE ID NO 12 is the amino acid sequence of the C-terminal region of OP-1.

SEQUENCE ID NO 13 is the amino acid sequence of the C-terminal region of BMP-5.

SEQUENCE ID NO 14 is the amino acid sequence of the C-terminal region of 60A.

SEQUENCE ID NO 15 is the amino acid sequence of the C-terminal region of BMP-2.

SEQUENCE ID NO 16 is the amino acid sequence of the C-terminal region of BMP-4.

SEQUENCE ID NO 17 is the amino acid sequence of the C-terminal region of DPP.

SEQUENCE ID NO 18 is the amino acid sequence of the C-terminal region of BMP-3.

SEQUENCE ID NO 19 is the amino acid sequence of the C-terminal region of MIS.

SEQUENCE ID NO 20 is the amino acid sequence of the C-terminal region of lnhibin-α.

SEQUENCE ID NO 21 is the amino acid sequence of the C-terminal region of Inhibin-βA.

SEQUENCE ID NO 22 is the amino acid sequence of the C-terminal region of Inhibin-βB.

SEQUENCE ID NO 23 is the amino acid sequence of the C-terminal region of TGF-β1.

SEQUENCE ID NO 24 is the amino acid sequence of the C-terminal region of TGF-β2.

SEQUENCE ID NO 25 is the amino acid sequence of the C-terminal region of TGF-β3.

SEQUENCE ID NO 26 is the amino acid sequence of the C-terminal region of TGF-β4.

SEQUENCE ID NO 27 is the amino acid sequence of the C-terminal region of TGF-β5.

SEQUENCE ID NO 28 is the nucleotide sequence of human GDF-3.

SEQUENCE ID NO 29 is the deduced amino acid sequence of human GDF-3.

I claim:

1. An antibody that binds to a polypeptide having an amino acid sequence as set forth in SEQ ID NO:6 or SEQ ID NO:29, and functional antibody fragments thereof.

2. The antibody of claim 1, wherein the antibody is polyclonal.

3. The antibody of claim 1, wherein the antibody is nonclonal.

4. The antibody of claim 3, wherein the antibody is humanized antibody.

UNITED STATES PATENT AND TRADEMARK OFFICE
CERTIFICATE OF CORRECTION

PATENT NO.    : 6,025,475
DATED         : March 24, 1998
INVENTOR(S)   : Lee et al.

It is certified that error appears in the above-identified patent and that said Letters Patent is hereby corrected as shown below:

Column 50,
Lines 1-2, please replace the present claim 3, which reads:

"3. The antibody of claim 1, wherein the antibody is nonclonal." with the following:

-- 3. The antibody of claim 1, wherein the antibody is monoclonal. --

Signed and Sealed this

Twenty-fourth Day of September, 2002

*Attest:*

*Attesting Officer*

JAMES E. ROGAN
*Director of the United States Patent and Trademark Office*